(12) United States Patent
Chase et al.

(10) Patent No.: US 10,195,187 B2
(45) Date of Patent: Feb. 5, 2019

(54) OXYBUTYNIN-XANOMELINE TRANSDERMAL THERAPEUTIC SYSTEM COMBINATIONS

(71) Applicant: Chase Pharmaceuticals Corporation, Parsippany, NJ (US)

(72) Inventors: Thomas N. Chase, Washington, DC (US); Kathleen E. Clarence-Smith, Washington, DC (US)

(73) Assignee: Chase Pharmaceuticals Corporation, Madison, NJ (US)

(*) Notice: Subject to any disclaimer, the term of this patent is extended or adjusted under 35 U.S.C. 154(b) by 0 days.

(21) Appl. No.: 15/556,197

(22) PCT Filed: Mar. 4, 2016

(86) PCT No.: PCT/US2016/020879
§ 371 (c)(1),
(2) Date: Sep. 6, 2017

(87) PCT Pub. No.: WO2016/144749
PCT Pub. Date: Sep. 15, 2016

(65) Prior Publication Data
US 2018/0050023 A1    Feb. 22, 2018

Related U.S. Application Data

(60) Provisional application No. 62/144,010, filed on Apr. 7, 2015, provisional application No. 62/129,279, filed on Mar. 6, 2015.

(51) Int. Cl.
| | | |
|---|---|---|
| A61K 31/4439 | (2006.01) |
| A61K 31/216 | (2006.01) |
| A61K 9/06 | (2006.01) |
| A61K 9/70 | (2006.01) |
| A61P 25/28 | (2006.01) |

(52) U.S. Cl.
CPC ............ *A61K 31/4439* (2013.01); *A61K 9/06* (2013.01); *A61K 9/7015* (2013.01); *A61K 9/7092* (2013.01); *A61K 31/216* (2013.01); *A61P 25/28* (2018.01); *A61K 9/703* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 5,980,933 A | 11/1999 | Bymaster et al. | |
| 6,562,368 B2 * | 5/2003 | Hsu ...................... | A61K 9/0014 424/443 |
| 2004/0057985 A1 | 3/2004 | Bracht | |
| 2011/0020423 A1 * | 1/2011 | Elenko ................. | A61K 9/4858 424/432 |
| 2014/0186428 A1 | 7/2014 | Aida et al. | |

OTHER PUBLICATIONS

Chase et al, "High Dose Donepezil Treatment of Alzheimer's Disease—Preliminary Results from CPC-201 and CPC-212 Trials", http://www.chasepharmaceuticals.com/blog/high-dose-donepezil-treatment-of-alzheimers-disease-poster-presented-on-december-9-by-thomas-n.-chase-md (Dec. 2015).
Written Opinion of the International Searching Authority of PCT/US2016/020879 dated May 23, 2016.
International Search Report of PCT/US2016/020879 dated May 23, 2016.

* cited by examiner

*Primary Examiner* — Heidi Reese
(74) *Attorney, Agent, or Firm* — Roy Isaac

(57) ABSTRACT

Transdermal therapeutic system and method of using the same for safely treating hypocholinergic disorders of the central nervous system such as Alzheimer type dementia. The transdermal therapeutic system comprises oxybutynin in combination with a cholinergic receptor agonist (CRA) such as xanomeline.

4 Claims, No Drawings

OXYBUTYNIN-XANOMELINE TRANSDERMAL THERAPEUTIC SYSTEM COMBINATIONS

CROSS-REFERENCE TO RELATED APPLICATIONS

This application is a National Stage of International Application No. PCT/US2016/020879, filed on Mar. 4, 2016, which claims benefit of U.S. Provisional Application No. 62/144,010, filed Apr. 7, 2015; and Provisional Application No. 62/129,279, filed Mar. 6, 2015; the entire disclosures of each of which are hereby incorporated herein by reference.

OBJECT OF THE INVENTION

The invention relates to a transdermal therapeutic system containing 4-diethylaminobut-2-ynyl 2-cyclohexyl-2-hydroxy-2-phenylethanoate, known under its International Non-proprietary name as oxybutynin, or a pharmaceutically acceptable salt thereof, for use in the treatment of Alzheimer type dementia, in combination with 3-[4-(Hexyloxy)-1,2,5-thiadiazol-3-yl]-1,2,5,6-tetrahydro-1-methylpyridine, known under its International Non-proprietary name as xanomeline, a Cholinergic Receptor Agonist (CRA). The invention also concerns use of such a transdermal therapeutic system in a method for enhancing the maximal efficacy and maximal tolerated dose of a CRA in a patient suffering from dementia of the Alzheimer type or of other types of hypocholinergic disorders of the nervous system.

The invention further relates to a transdermal therapeutic system comprising both oxybutynin and xanomeline, or a pharmaceutically acceptable salt thereof. In particular, the transdermal therapeutic system involves delivering a combination of oxybutynin with a high dose of xanomeline via transdermal formulation(s) and transdermal patches incorporating such formulations.

The present invention also relates to transdermal drug formulations, transdermal patches incorporating such formulations, as well as associated methods of use for treatment of Alzheimer type dementia and other types of hypocholinergic disorders of the nervous system. The formulations of the present invention can be incorporated into patches for transdermal administration. For instance, a transdermal patch for transdermal delivery of oxybutynin and a transdermal patch for transdermal delivery of a CRA, preferably, xanomeline.

DEFINITIONS

"Peripheral": refers to anticholinergic agents that are largely unable (have a limited ability) to enter the central nervous system following systemic administration and thus do not affect brain function to a clinically appreciable degree. These drugs can include both quaternary and tertiary ammonium anticholinergic agents, especially se having low lipid solubility.

"Anticholinergic therapy": the treatment with an anticholinergic agent of such medical conditions as gastro-intestinal cramping, nausea, retching, vomiting, fecal incontinence, bladder spasms, urinary incontinence, overactive bladder, asthma, motion sickness, muscular spasms, and smooth muscle contractive disorders; or the treatment with an anticholinergic agent of side effects caused by xanomeline and other CRAs, including, but not limited to gastro-intestinal cramping, nausea, retching, vomiting, fecal incontinence, bladder spasms, urinary incontinence, overactive bladder, asthma, motion sickness, muscular spasms, and smooth muscle contractive disorders.

"CNS": Central Nervous System.
"AChR": Acetylcholine Receptor.
"CRA": Cholinergic Receptor Agonist.
"PNS": Peripheral Nervous System.
"CSF": Cerebrospinal Fluid.
"IR": Immediate Release of the active ingredient from a composition.
"ER": Extended. Release (or sustained or controlled release) of the active ingredient from a composition by any administration route.
"AChEI(s)": Acetyl Choline Esterase Inhibitor(s).
"NsPAChA(s)": non-selective, peripheral AntiCholinergic Agent(s).
"Non selective": refers to nsPAChAs, and applies to anticholinergic agents exhibiting inhibitory activity broadly across the various subtypes of muscarinic M-receptors, namely the M1-M5 receptors.
"Muscarinic type receptors (mAChRs)": Five subtypes of muscarinic receptors, M1 through M5, have been identified.
"Transdermal delivery" of drug can be targeted to skin tissues just under the skin, regional tissues or organs under the skin, systemic circulation, and/or the central nervous system.
"Transdermal therapeutic system" is targeted to delivery of drug to skin tissues just under the skin, regional tissues, using transdermal drug formulations and transdermal patches incorporating such transdermal drug formulations.

BACKGROUND OF THE INVENTION

Reduced levels of neurotransmitters including acetylcholine occur in dementias of the Alzheimer type. In particular, a deficit in acetylcholine-mediated transmission is thought to contribute to the cognitive and neurobehavioral abnormalities associated with these disorders. Accordingly, drugs known to augment cholinergic transmission in the CNS are the mainstay of current therapy. In addition, other diseases of the nervous system also involve decreased cholinergic transmission and are referred to as "hypocholinergic syndromes of the nervous system." Such diseases include, but are not limited to, Mild Cognitive Impairment (MCI), Lewy Body Disease dementia (LBD), Parkinson disease dementia (PDD), post-stroke dementia, vascular dementia, Traumatic Brain Injury, Down's syndrome, Anorexia Nervosa, and schizophrenia. It is well documented that schizophrenic patients experience cognitive disturbances that are not well addressed by current medications (reviewed in Foster et al, 2014). CRAs have been reported to dose-dependently improve the cognitive disturbances associated with schizophrenia, but the effect of CRAs is of limited size and dose-dependent side effects prevent further increases in the CRA doses.

Acetylcholinesterase inhibitors (AChEIs) are now not only part of the standard of care for patients suffering from a dementia of the Alzheimer type, but are also widely used off-label for various other chronic progressive hypocholinergic disorders of the nervous system. AChEIs have the enhancement of acetylcholine-mediated neurotransmission as a general mechanism of action. All act in the human CNS to increase and prolong the availability of acetylcholine by inhibiting its degradatory enzyme acetylcholinesterase (AChE). Four AChEIs have been approved by the U.S. FDA for the treatment of dementias of the Alzheimer type: tacrine, donepezil [Aricept®], rivastigmine [Exelon®] and galantamine [Razadyne®]. Rivastigmine has also been approved for the treatment of Parkinson's disease dementia. AChEIs are available in various formulations including immediate release forms such as tablets, capsules and solutions as well as rapid dissolving and extended release forms for oral administration as well as those for parenteral (e.g. transdermal) administration.

Unfortunately, however, none of the currently available AChEIs offers more than modest clinical benefit for patients suffering from any of the aforementioned dementing disorders, even when these medications are administered at their maximum safe and tolerated doses. This is the first problem limiting the success of current AChEI therapy of Alzheimer type dementias.

A second problem limiting the success of current AChEI therapy of Alzheimer type dementias is that, even at recommended amounts, all these drugs produce dose limiting adverse reactions, mainly if not exclusively, by over-stimulating peripheral cholinergic receptors of the muscarinic type. As a result, signs and symptoms of untoward gastrointestinal, pulmonary, cardiovascular, urinary, and other systems dysfunction occur. These side effects commonly include, anorexia, nausea, vomiting, diarrhea, abdominal pain, weight loss; increased bronchial secretions, dyspnea, bronchoconstriction and bronchospasm; bradycardia, supraventricular cardiac conduction abnormalities, vasodilation, hypotension, dizziness and syncope; urinary bladder spasm, increased urinary frequency, and incontinence; flushing and diaphoresis; fatigue, headache, lacrymation, miosis, and loss of binocular vision (Physicians' Desk Reference 2008, Thomson P D R, Montvale, N.J.).

These problems linked to the use of the AChEIs have been solved by combining said AChEI with a nsPAChA (U.S. Pat. No. 8,404,701) or with a non-anticholinergic antiemetic agent (U.S. Pat. No. 8,877,768), these combination allowing a great increase of the administered AChEI doses with attending increase in plasma and brain concentrations of the AChEI, and consequent possibility of increasing anti-dementia efficacy.

Another way to increase the cholinergic transmission in the brain is to stimulate post-synaptic cholinergic receptors by administering an agonist of the muscarinic receptors, but the results were generally disappointing. However, the efficacy of one such product, xanomeline, that stimulates muscarinic receptors in the brain and in the periphery was studied in patients with Alzheimer disease in a 6-month double-blind, placebo-controlled, parallel group trial. Compared to placebo, xanomeline was shown to significantly improve cognitive and behavioral symptoms of Alzheimer disease (Bodick et al, 1997), but also caused dose-dependent unacceptable side effects, including bradycardia, gastrointestinal distress, excessive salivation, and sweating. Such side effects prevented the use of doses of xanomeline that could achieve maximum anti-dementia efficacy and reflect stimulation of cholinergic receptors outside the brain. As described in the present invention, utilizing a drug that can antagonize the dose-limiting adverse events of a CRA without preventing anti-dementia efficacy enables the frill antidementia efficacy of the CRA.

Dose-limiting adverse events attending the use of drugs that stimulate cholinergic transmission, such as xanomeline, appear to primarily reflect the excessive stimulation of peripheral cholinergic receptors, especially those of the muscarinic type (mAChRs), such that in both healthy volunteers and Alzheimer's patients many of these side effects have been reported for xanomeline; in the patient population this led to a discontinuation rate higher than 50% while the effects on cognition were not as robust and mainly seen at the highest doses tested (Mirza et al. CNS Drug Reviews Vol. 9, No. 2, pp. 159-186, 2003). These authors suggest that xanomeline could be a good antipsychotic.

The literature does not teach how to take advantage of the ubiquitous, potent activity of the muscarinic agonists safely. Thus, the problem of the effective and safe treatment of Alzheimer type dementia and in general of hypocholinergic disorders in the CNS such as schizophrenia, Down's syndrome, Tourette disease, tardive dyskinesia, Pick's disease, Huntington's chorea, and Friedrich's ataxia, with a muscarinic agonist, remains of primary importance.

An improvement in the treatment of Alzheimer type dementia is attained by a combined therapy associating a non-selective, peripheral anticholinergic agent, at a dose of from 20% to 200% the current daily doses, with an AChEI, at a dose up to about 6 times the maximal recommended dose of said AChEI, as disclosed in U.S. Pat. No. 8,404,701, the disclosure of which is herein incorporated by reference in its entirety. By such a treatment, a higher acetylcholinesterase inhibition in the CNS is achieved and greater relief of the symptoms of Alzheimer type dementia is enabled, by concomitantly decreasing concurrent adverse effects.

In addition, U.S. Pat. No. 8,877,768, the disclosure of which is herein incorporated by reference in its entirety, discloses an improvement in the treatment of Alzheimer type dementia, which is attained by a combined therapy associating a non-anticholinergic-antiemetic agent, at a dose of from 50% to 300% the current IR daily doses, with an AChEI, at a dose up to 4 times the maximal recommended doses of said AChEI when administered alone.

Similarly, WO 2014/039627, the disclosure of Which is herein incorporated by reference in its entirety, discloses the discovery of the property of the non-selective, peripheral anticholinergic agent of increasing the blood levels of a concurrently administered AChEI, the higher being the dose of either the non-selective anticholinergic agent or the AChEI, the higher being the increase of the AChEI blood levels. Thus, this document recommends the use of high doses of both the non-selective, peripheral anticholinergic agent and of the AChEI in order to ameliorate the symptoms of Alzheimer's dementia. In particular, this document states that "[w]hile potentially lessening side effects and thereby enabling the use of higher and thus more effective doses of the AChEI, merely employing the concomitant use of antiemetics, such as domperidone and others, or of anticholinergics such as propantheline, oxybutynin, tolterodine and others, falls short of achieving the utmost therapeutic advantages of AChEIs in the treatment Alzheimer type dementias".

Thus, U.S. Pat. No. 8,404,701 and, especially, WO 2014/039637 specifically exclude anticholinergic agents which are selective and/or non-peripheral because selective agents are not able to counteract the whole spectrum of the AChEIs' adverse effect and, worse, the non-peripheral anticholinergics, such as oxybutynin, are able to dangerously counteract the beneficial central action of said AChEIs.

The literature discloses pharmaceutical compositions and Transdermal Therapeutic Systems (TTS) delivering oxybutynin through the human skin.

For example, U.S. Pat. No. 5,441,740 and U.S. Pat. No. 5,500,222, the disclosures of which are herein incorporated by reference in their entirety, disclose a patch for the transdermal administration of oxybutynin base using a monoglyceride or a mixture of monoglycerides of fatty acids as skin permeation-enhancer.

U.S. Pat. No. 5,686,097; U.S. Pat. No. 5,747,065; U.S. Pat. No. 5,750,137 and U.S. Pat. No. 5,900,250, the disclosures of which are herein incorporated by reference in their entirety, disclose a patch for the transdermal administration of oxybutynin base using a monoglyceride or a mixture of monoglycerides plus a lactate ester as skin permeation-enhancer.

A similar patch, adding a non-rate controlling tie layer on the skin-proximal surface of the reservoir, not affecting the drug release, is described in U.S. Pat. No. 5,614,211 and U.S. Pat. No. 5,635,203, the disclosures of which are herein incorporated by reference in their entirety.

U.S. Pat. No. 5,212,199, U.S. Pat. No. 5,227,169, U.S. Pat. No. 5,601,839 and U.S. Pat. No. 5,834,010, the disclosures of which are herein incorporated by reference in their entirety, disclose a patch for transdermal administration of basic drugs using triacetin as permeation enhancer.

U.S. Pat. No. 6,555,129, the disclosure of which is herein incorporated by reference in its entirety, discloses a TTS substantially consisting of an oxybutynin-containing matrix mass in the form of a layer which is self-adhesive, and in which the matrix mass consists of ammonium-group-containing (meth)acrylate copolymers, at least one citric acid triester and 5-25% by weight of oxybutynin.

U.S. Pat. No. 6,562,368, the disclosure of which is herein incorporated by reference in its entirety, discloses a method for transdermally administering oxybutynin using a composition in form of a patch, a cream, a gel, a lotion or a paste comprising oxybutynin and a hydroxide-releasing agent substantially consisting of inorganic hydroxides, inorganic oxides, metal salts of weak acids, and mixtures thereof.

U.S. Pat. No. 6,743,441; U.S. Pat. No. 7,081,249; U.S. Pat. No. 7,081,250; U.S. Pat. No. 7,081,251; U.S. Pat. No. 7,081,252 and U.S. Pat. No. 7,087,241, the disclosures of which are herein incorporated by reference in their entirety, disclose a transdermal patch delivering a composition comprising oxybutynin to a subject to provide a plasma area under the curve ratio of oxybutynin to an oxybutynin metabolite of from about 0.5:1 to about 5:1, optional in the presence of a permeation enhancer.

U.S. Pat. No. 7,029,694; U.S. Pat. No. 7,179,483; U.S. Pat. No. 8,241,662 and US 2009/0018190, the disclosures of which are herein incorporated by reference in their entirety, disclose a transdermal gel formulation comprising oxybutynin providing a plasma area under the curve ratio of oxybutynin to an oxybutynin metabolite of from about 0.5:1 to about 5:1, optional in the presence of a permeation enhancer.

US 2004/0219194, the disclosure of which is herein incorporated by reference in its entirety, discloses a transdemial therapeutic system containing oxybutynin, triacetin and Aloe vera extract as permeation enhancer.

US 2004/0057985, the disclosure of which is herein incorporated by reference in its entirety, discloses transdermal therapeutic systems (TTS) for the administration of oxybutynin with which therapeutically active absorption rates can be achieved without the necessity of adding permeation-enhancing substances. These TTS comprise a substantially water vapor-impermeable backing layer, at least one pressure-sensitive adhesive matrix layer attached thereto, and a detachable protective film, said matrix layer comprising an inner phase containing the active substance oxybutynin, and an outer, pressure sensitive adhesive phase based on hydrocarbon polymers or/and silicone polymers.

US 2005/0064037, the disclosure of which is herein incorporated by reference in its entirety, discloses an oxybutynin gel formulation topical gel formulation comprising oxybutynin chloride salt, a short chain alcohol, a gelling agent substantially consisting of high-molecular-weight, cross-linked polymer of acrylic acid or cross-linked copolymer of acrylic acid and C10-30 alkyl acrylate, and optionally a permeation enhancer substantially consisting of propylene glycol, propylene glycol laurate, isopropyl myristate, and methyl lactate.

WO 2005/039531, US2007/022379, US 2010/0216880, US 2014/0037713 and U.S. Pat. No. 8,652,491, the disclosures of which are herein incorporated by reference in their entirety, disclose a transdermal or transmucosal pharmaceutical formulation, that can be utilized for topical or transdermal application, such that solutions, creams, lotions, sprays, ointment, gels, aerosols and patch devices, for the delivery of one or more active agents, including anticholinergics, in particular oxybutynin. Said formulation includes oxybutynin in a solvent system comprising a diethylene glycol monoalkyl ether and a glycol in specific ratios, alcohol and water. In particular, according to U.S. Pat. No. 8,652,491 a possible secondary active agent, in addition to the anti-cholinergic agent such as oxybutynin, may be an antiperspirant, a tranquilizer or another agent capable of ameliorating hyperhidrosis. In addition, according to WO 2005/039531 the active agent may also be selected from an anti-Alzheimer's drug, in particular galantamine, rivastigmine, donepezil, tacrine, or memantine, without giving any indication of the doses to be used.

WO 2005/107812, U.S. Pat. No. 7,425,340 and US 2008/0260842, the disclosures of which are herein incorporated by reference in their entirety, disclose formulations containing an anticholinergic agent, in particular oxybutynin, in admixture with urea, urea congeners or urea-containing compounds as permeation enhancers.

WO 01/07018 and U.S. Pat. No. 8,420,117, the disclosures of which are herein incorporated by reference in their entirety, disclose a matrix patch formulation containing no water for external use, comprising, as essential components oxybutynin hydrochloride, citric acid and sodium acetate.

WO2013/061969 and US 2014/0271796, the disclosures of which are herein incorporated by reference in their entirety, disclose a transdermal absorption preparation comprising at least one drug selected from oxybutynin and pharmaceutically acceptable salts thereof; and a sterol such as cholesterol, cholesterol derivatives and cholesterol analogs.

U.S. Pat. No. 8,802,134, the disclosure of which is herein incorporated by reference in its entirety, discloses a method for producing a patch wherein oxybutynin is incorporated in an adhesive agent layer composition comprises the acrylic-based polymer as the adhesive base agent, and the acrylic-based polymer is a copolymer of polymethyl methacrylate with a polyacrylate.

U.S. Pat. No. 8,877,235, the disclosure of which is herein incorporated by reference in its entirety, discloses a patch consisting of a support layer and of an adhesive agent layer arranged on the at least one surface of the support layer, the adhesive agent layer comprising oxybutynin hydrochloride in a supersaturated concentration in a dissolved form. Said layer also comprises acrylic-based polymers and rubber-based polymers, as adhesive base agents, and liquid paraffin, a sterol, an organic acid, and a tackifier.

The disclosures of the aforementioned documents are incorporated herein by reference in their entirety.

Oxybutynin is a well-known non-selective anticholinergic medication used to relieve urinary and bladder difficulties, including frequent urination and urge incontinence and all the above references emphasize this use. However, as set forth above, oxybutynin is not "peripheral" as per the definition given above because it is able to cross the blood brain barrier ("BBB") to a non-negligible extent (Rebecca J MeCrery and Rodney A Appell, Ther Clin Risk Manag. March 2006; 2/1: 19-24).

Oxybutynin is commercially presented in a patch releasing 3.9 mg/day oxybutynin (OXYTROL®). This patch provides significant improvements in all the measured parameters with less systemic adverse effects, as summarized by J. Jayarajan and S. B. Radomski in a review presented on 4 Dec. 2013: "Pharmacotherapy of overactive bladder in adults: a review of efficacy, tolerability, and quality of life" (J. Jayarajan et al., Research and Reports in Urology 2014:6), the disclosure of which is herein incorporated by reference in its entirety. However, oxybutynin is anyway deemed to cross the BBB owing to its high lipophilicity, neutrality, and small molecular size (C. A. Donnellan et al. BMJ 1997; 315:1363-4; R. Scheife and M. Takeda, (Clin Ther. 2005; 27:144-53). the disclosure of which is herein incorporated by reference in its entirety.

Oxybutynin is also commercially presented (GELNIQUE®) in a TTS consisting of a hydroalcoholic gel containing 100 mg oxybutynin chloride per gram of gel and available in a 1 gram (1.14 ml) unit dose. This TTS is deemed to have a pharmacokinetic profile similar to that of the patch delivery system, while producing lower N-desetyloxybutynin metabolite plasma concentrations (Vincent R. Lucente et al.; Open Access Journal of Urology 2011/3, 35-42). Another commercial TTS system, presents oxybutynin in a hydroalcoholic gel containing 30 mg oxybutynin base per gram of gel and is available (ANTUROL®) in a 0.92 gram (1 mL) unit dose that contains 28 mg oxybutynin per gram of gel. Also Anturol® demonstrated plasma levels of oxybutynin comparable to the efficacious plasma levels observed for oral and patch therapies with lower N-desethyloxybutynin plasma levels (Anturol® Gel Summary by Antares Pharma).

Oxybutynin is a very good tool for administering anticholinergic therapy but, even when given by transdermal route, it is deemed to induce adverse effects in the CNS, as per the warning which is present in the OXYTROL® label and as reported in the literature. Indeed the current FDA product label for transdermal oxybutynin (Oxytrol®) states that nervous system side effects of Oxytrol® may include: Very common (10% or more): Dizziness, somnolence; Common (1% to 10%): Headache, mental/mood changes (such as confusion), insomnia, nervousness, convulsions, dysgeusia; and frequency not reported: paralysis, coma, CNS excitation. It further lists Central Nervous System Effects under Warnings and Precautions: "Products containing oxybutynin are associated with anticholinergic central nervous system (CNS) effects. A variety of CNS anticholinergic effects have been reported, including headache, dizziness, and somnolence. Patients should be monitored for signs of anticholinergic CNS effects, particularly after beginning treatment." In addition, the label states that overdosage with oxybutynin has been associated with anticholinergic effects including CNS excitation and that CNS symptoms of overdose may include: memory loss, confusion, convulsions, dizziness, and drowsiness (severe). This possibility becomes a-priori a material risk if it is intended to be used for the treatment of Alzheimer type dementia in combination with a CRA such as xanomeline, due to the competitive action of the two drugs inside the CNS.

U.S. Pat. No. 5,980,933 discloses a transdermal xanomeline patch formulation comprising an effective amount of xanomeline, from 0.1 to 10 parts by weight azone, from 30 to 69.8 parts ethanol, 29 to 50 parts by weight water, from 0 to 30 parts by weight propylene glycol, and 1 to 5 parts by weight Klucel HF, also with about 70 to 99.8% acrylate adhesive. The literature only specifies that such a patch should have less adverse effects compared with the oral forms.

US 2011/0020423 discloses the combination of one or more muscarinic "Activators" (e.g., agonist, partial agonist, co-agonist, physiological agonist, potentiator, stimulator, allosteric potentiator, positive allosteric modulator or allosteric agonist) and one or more muscarinic "Inhibitors" (e.g., antagonist, partial antagonist, competitive antagonist, non-competitive antagonist, uncompetitive antagonist, silent antagonist, inverse agonist, reversible antagonist, physiological antagonist, irreversible antagonist, inhibitor, reversible inhibitor, irreversible inhibitor, negative allosteric modulator, or allosteric antagonist).

U.S. Pat. No. 8,853,219 discloses muscarinic agonists, which are useful for stimulating muscarinic receptors and treating cognitive disorders, said agonists including oxadiazole and oxathiazole derivatives, in particular 5-(3-ethyl-1,2,4-oxadiazol-5-yl)-1,4,5,6-tetrahydropyrimidine, also known as MCD-386, which is described in the literature for example in U.S. Pat. No. 5,403,845 to Dunbar, et al., 3-Methyl-5-(piperidin-3-yl)-1,2,4-oxadiazole), as a racemic mixture and as the single stereoisomers. This document also discloses combination compositions and co-administration comprising muscarinic agonists and antagonists, said muscarinic agonists including the substituted oxadiazoles and thiadiazoles disclosed therein and said muscarinic antagonists including atropine sulfate, N-methylatropine nitrate, flavoxate hydrochloride, N-methylscopolamine hydrochloride (methscopolamine), oxybutinin chloride, glycopyrrolate bromide, darifenacin hydrobromide, solifenacin succinate, propantheline bromide, trospium chloride, tolterodine tartrate, fesoterodine fumarate, methantheline bromide and combinations thereof. In terms of co-administration of a muscarinic-antimuscarinic combination, this document intends separate administration of agonist and antagonist, e.g., in separate dosage forms such as separate pills, separate injectable solutions or separate iontophoretic patches. According to this document, pharmacological tests made with a combination of representative oxadiazoles muscarinic agonists with muscarinic antagonists showed that darifenacin and oxybutinin, both tertiary amines, are less effective than the other muscarinic antagonists by both oral and iontophoretic patch administration. In addition, this document observes that these drugs are known to penetrate the blood-brain barrier and may therefore inhibit the therapeutic effects of the agonist in the brain.

In summary notwithstanding great scientific effort, the problem of the safe treatment of hypocholinergic disorders of the nervous system such as Parkinson's dementia, Lewy body diseases, Down Syndrome, and chronic neuropathic pain remains unsolved.

SUMMARY OF THE INVENTION

It has now been found that it is possible to safely administer high doses of xanomeline in combination with currently available transdermal therapeutic systems without inducing central adverse effects and without inducing peripheral cholinergic side effects.

The finding of the present invention was unexpected in view of the disclosures of the art, in particular in view of the knowledge of, on one side, the lack of efficacy of the muscarinic cholinergic receptor agonists at the doses administered to the patients and, on the other side, of the irreducible adverse effects induced by the products at said administered doses. On the contrary, it has been found that the administration of xanomeline concurrently with an oxybutynin transdermal system, will not produce any adverse effect not only at the xanomeline doses normally administered to a human, but also at doses which would be unquestionably intolerable for said human More specifically, it has been observed that, contrary to the disclosure of U.S. Pat. No. 8,853,219, a TTS comprising oxybutynin, when administered in combination with a TTS comprising xanomeline, not only counteracts the adverse effects of xanomeline but also allows the administration of xanomeline doses that would not have been tolerated if xanomeline were administered alone.

Finally, most surprisingly, it has been found that transdermally administered oxybutynin is not associated with adverse cognitive effects, and enables a safe increase of muscarinic receptor stimulation due to the action of the muscarinic agonist.

In summary, the invention provides a new tool for treating Alzheimer type dementia by enabling the full efficacy of CRAB. Said new tool comprises treating a patient in need of such a treatment with a transdermal therapeutic system comprising oxybutynin, in combination with transdermal CRAs, such as preferably, xanomeline. This treatment occurs, on one hand without the onset of xanomeline-associated peripheral dose-limiting adverse effects and, on the other hand, without the onset of oxybutynin central adverse effects.

According to the present invention, it is also possible to equilibrate the transdermal oxybutynin dose and the transdermal xanomeline doses in order to attain the maximum efficacy with reduced risk of both central and peripheral adverse effects, by using a transdermal therapeutic system containing a predetermined dose of oxybutynin or a pharmaceutically acceptable salt thereof, concurrently with a predetermined daily dose of xanomeline or of a pharmaceutically acceptable salt thereof.

An embodiment of the invention relates to a method for treating Alzheimer type dementia, which comprises administering to a patient in need of said treatment a transdermal therapeutic system comprising oxybutynin or pharmaceutically acceptable salt thereof, in combination with xanomeline or pharmaceutically acceptable salt thereof.

In one embodiment of the method, the oxybutynin in the transdermal therapeutic system is in a patch delivering oxybutynin at a rate of 3.9 mg/24 hours and the xanomeline in the transdermal therapeutic system is in a patch globally delivering xanomeline in daily doses of 1.2 to 6 times the maximum tolerated dose of the transdermal xanomeline given alone.

In one embodiment of the method, the transdermal therapeutic system delivers oxybutynin at a rate of 3.9 mg/24 hours and is combined with a daily dose of xanomeline from 1.5-times to 6-times the highest tolerated dose when oral xanomeline is given alone.

Another embodiment of the invention relates to a transdermal therapeutic system comprising oxybutynin or pharmaceutically acceptable salt thereof in combination with a CRA at a dose level from 1.5-times to 6-times the highest tolerated dose when the CRA is given alone.

In one embodiment of the transdermal therapeutic system, the oxybutynin or pharmaceutically acceptable salt thereof is in a transdermal formulation.

In another embodiment of the transdermal therapeutic system, the CRA is xanomeline or pharmaceutically acceptable salt thereof in a transdermal formulation.

In a preferred embodiment of the transdermal therapeutic system, the transdermal formulation for each of oxybutynin or pharmaceutically acceptable salt thereof and xanomeline or pharmaceutically acceptable salt thereof is incorporated into a patch.

DETAILED DESCRIPTION

The present invention provides a transdermal therapeutic system that may be used for the treatment of hypocholinergic disorders of the central nervous system, including but not limited to, Alzheimer type dementia (including but not limited to Parkinson's disease dementia and Frontotemporal Lobar Dementia), Mild cognitive Impairment (MCI), Vascular Dementia Traumatic Brain Injury, Down's Syndrome, Anorexia nervosa, and Schizophrenia.

In particular, the present invention provides a transdermal therapeutic system comprising oxybutynin, or a pharmaceutically acceptable salt thereof, for its use in the treatment of dementia of Alzheimer type, in combination with a CRA transdermally administered at a high dose. In particular a dose of CRA from 1.5 times to 6 times higher than the daily maximal dose that causes unacceptable side effects.

Preferably, the CRA is xanomeline as a TTS component that delivers a steady state plasma concentration of xanomeline in a patient (the "Xanomeline TTS Delivery Rate") that is an effective amount up to 4 times higher than the peak plasma concentration of xanomeline observed with the first intolerable dose of oral xanomeline in the patient being treated (where the intolerable oral xanomeline dose is determined without the use of oxybutynin or similar drugs). Oxybutynin TTS may contain oxybutynin or a pharmaceutically acceptable salt thereof in an amount allowing an oxybutynin release of 3.9 mg/24 h, or from 3.9 mg/24 h to 5.85 mg/24 h or from 3.9 mg/24 h to 7.8 mg/24 h. In the TTS in form of a patch, both oxybutynin and xanomeline are preferably used as the base thereof.

Said oxybutynin/xanomeline combination may also be administered in a single TTS containing the two active ingredients in admixture each other in the same TTS or separated in the same patch in two different TTSs each delivering the aforementioned oxybutynin and xanomeline daily doses.

According to an embodiment, the present invention provides a method for treating a patient suffering from an Alzheimer type dementia or other hypocholinergic syndrome of the nervous system, or suffering from schizophrenia which comprises daily administering to said patient a transdermal therapeutic system comprising oxybutynin, or a pharmaceutically acceptable salt thereof, in combination with a CRA selected from the group consisting of xanomeline and pharmaceutically acceptable salts thereof.

The invention also provides an oxybutynin TTS consisting of a patch daily releasing from 3.9 mg to 7.8 mg per day, in particular from 3.9 mg/24 h to 5.8 mg/24 h, especially 3.9 mg/24 h, of oxybutynin for use for the treatment of Alzheimer type dementia in combination with transdermal xanomeline.

The oxybutynin TTS for use according to the present invention may be in any oxybutynin delivering transdermal pharmaceutical form, such as a patch, a gel, a cream, a spray, an ointment, a lotion or a paste, wherein oxybutynin is present in admixture with the common diluents and permeation enhancers, said pharmaceutical form containing oxybutynin base or a pharmaceutically acceptable salt thereof, such as its hydrochloride, hydrobromide, sulfate, phosphate, mesilate, acetate, maleate, succinate, lactate, citrate, hydrogen tartrate, tartrate, napsilate or embonate.

The permeation enhancer may be any compound that allows the improved permeation of drugs through the skin (see for example the review in Pharmaceutical Technology, November 1997, pages 58-66, the disclosure of which is herein incorporated by reference in its entirety). Such substances may be lower ($C_1$-$C_4$) alkanols; fatty alcohols such as lauryl alcohol (dodecanol), alone or in combination with a lower alkanol; fatty acids such as linolenic acid or oleic acid; fatty acid esters such as isopropyl palmitate, stearate, linoleate, oleate or myristate; glycerol; glycerol monoesters such as glycerol monostearate, monolinoleate or monooleate; glycerol diesters; glycerol triesters such as triacetin; sucrose monostearate, monolinoleate or monooleate; sorbitan esters; fatty alcohol ethers having from 10 to 20 carbon atoms; glycols, such as diethylene glycol or propylene glycol; glycols lower alkyl ethers, such as diethylene glycol mono($C_2$-$C_4$)alkyl ether, in particular diethylene glycol monoethyl ether.

These permeation enhancers are present in an amount from 0.01 to 20% by weight of the total weight of the composition, advantageously in an amount of from 0.05 to 10% by weight, preferably from 0.1 to 5% by weight.

Advantageously, the oxybutynin TTS releases 3.9-5.85 mg/day of oxybutynin, administered in combination with xanomeline. The preferable combination is an oxybutynin patch delivering 3.9 mg/day of oxybutynin and transdermal xanomeline delivered at the Xanomeline TTS Delivery Rate.

In particular, a TTS consisting of a patch is obtained as described for example in U.S. Pat. No. 5,212,199, U.S. Pat. No. 5,227,169, U.S. Pat. No. 5,747,065, U.S. Pat. No. 6,743,441, U.S. Pat. No. 7,081,249, U.S. Pat. No. 7,081,250, U.S. Pat. No. 7,081,251, U.S. Pat. No. 7,081,252, U.S. Pat. No. 7,087,241, US 2004/0057985 U.S. Pat. No. 8,420,117, US 2014/0271796, U.S. Pat. No. 8,802,134, U.S. Pat. No. 8,877,235, the disclosures of which are each incorporated herein by reference in their entirety.

Typically, a TIS in form of a patch is manufactured by mixing a predetermined amount of oxybutynin, of xanomeline or of an association of the two drugs with the aforementioned permeation enhancer in a laminated composite which basically contains at least one reservoir comprising a adhesive which is a pressure-sensitive adhesive suitable for the contact with the skin, a backing layer and a strip to be removed just before the application of the patch on the subject's skin. The oxybutynin TTS may be manufactured according to one of the methods illustrated in the above-cited patent documents.

A TTS consisting of non-occlusive topical formulation for transdermal administration of oxybutynin is obtained as described for example in EP 0966972, U.S. Pat. No. 4,889, 845, U.S. Pat. No. 6,962,691, US 2003/0170194, US 2005/ 0064037, US 2006/0147383, U.S. Pat. No. 7,029,694, U.S. Pat. No. 7,179,483, US 2009/0018190, U.S. Pat. No. 8,241, 662, US 2007/0225379, US 2010/216880, U.S. Pat. No. 8,652,491, U.S. Pat. No. 7,425,340, U.S. Pat. No. 7,214,381, U.S. Pat. No. 7,470,433, US 2008/0260842, US 2014/ 0037713, the disclosures of which are each incorporated herein by reference in their entirety.

Typically, a TTS in form of a solution, cream, lotion, spray, ointment, gel, is manufactured by mixing a predetermined amount of oxybutynin or of a pharmaceutically acceptable salt thereof; of xanomeline or of a pharmaceutically acceptable salt thereof; or of an association of the two drugs, with common pharmaceutically acceptable carriers or vehicles and, optionally, with a permeation enhancer, of a gelling agent or thickening agent.

In one embodiment, a water-based gel formulation comprises 0.5-5% (w/w) of a pharmaceutically acceptable oxybutynin salt; 10-80% (w/w) of a lower ($C_2$-$C_4$) alkanol; and 0.2-2.0% of thickening agent and a basic pH regulator. The preferred short chain alcohols are ethanol and isopropanol. The preferred gelling/thickening agents include cross-linked polymer of acrylic acid with a high molecular weight, for example cross-linked copolymer of acrylic acid and ($C_{10}$-$C_{30}$)-alkyl acrylate, carboxymethylcellulose, hydroxypropylcellulose. In addition, in addition, the gel formulation comprises the permeation enhancers at from 0.01% to 20% by weight of the total weight of the composition, advantageously from 0.05% to 10% by weight, preferably from 0.1% to 5% by weight. Preferred permeation enhancer is glycerol or a monoester, diester or triester thereof, such as triacetin.

In another embodiment, a water-based gel formulation comprises 0.5-5% (w/w) of oxybutynin base; 10-80% (w/w) of a lower ($C_2$-$C_4$) alkanol; and 0.2-2.0% of a thickening agent. In addition, the gel formulation comprises the permeation enhancers at from 0.01% to 20% by weight of the total weight of the composition, advantageously from 0.05% to 10% by weight, preferably from 0.1% to 5% by weight. The suitable permeation enhancers are those listed above, preferably being propylene glycol, mono ($C_1$-$C_4$)-alkylated diethyleneglycol, propylene glycol laurate, isopropyl myristate, and methyl lactate.

In another embodiment, a TTS in form of a sprayable composition comprising oxybutynin or a pharmaceutically acceptable salt thereof in an aqueous or non-aqueous solution. Typically, a non-aqueous sprayable composition is an alcoholic solution in at least one ($C_2$-$C_4$)alkanol, containing oxybutynin or a pharmaceutically acceptable salt thereof in an amount of 0.5%-5% w/w, in respect of the total weight of the composition, from 20% to 90% w/w of a volatile silicone consisting of a linear or cyclic permethyl(tetra-deca)siloxane, such as hexamethyldisiloxane, octamethyltrisiloxane, decamethyltetrasiloxane, octamethylcyclotetrasiloxane and decamethylcyclopentasiloxane, and 0% to 15% of a permeation enhancer as defined above. The preferred volatile silicones are hexamethyldisiloxane (for example the product provided by Dow Corning®, DC Fluid 0.65 cSt), optionally containing silicone gum (for example the product provided by Dow Corning®, DC Silmogen Carrier), and octamethyltrisiloxane.

The formulation is obtained by mixing the various compounds mentioned below until a homogeneous and clear solution is obtained and the solution can be sprayed by a mechanical sprayer which mechanically pumps the compositions from a container, preferably in a metered dose, by conventional mechanisms through a nozzle which can directed at the desired site of application. The amount of propellant gas is regulated in order to propel the exact amount of oxybutynin.

Advantageous ER administration formulations are in form of a transdermal patch manufactured according to known technologies, for administering xanomeline base continuously and transdermally through a selected area of intact skin in a controlled manner for a prolonged period of time to induce high xanomeline blood levels in a human subject, in particular in a patient suffering from a dementia of Alzheimer type or a hypocholinergic disorder of the nervous system, said subject or patient being treated with said xanomeline.

Carriers and vehicles for transdermal formulations include retardant materials such as acrylic and methacrylic acid polymers and copolymers; cellulose derivatives such as hydroxypropylmethylcellulose, hydroxyethylcellulose, hydroxypropylethylcellulose, hydroxypropylcelluloses, methylcellulose, ethylcellulose, or sodium carboxymethylcellulose; gums; waxes; glycerides or aliphatic alcohols or a mixture thereof.

In particular, the transdermal therapeutic system comprises oxybutynin and is combined with xanomeline, said xanomeline being in a transdermal formulation and being delivered at the Xanomeline TTS Delivery Rate According to a preferred embodiment, the invention provides a TTS capable of concurrently delivering both oxybutynin and xanomeline, as depicted above.

Specifically, said TTS is a patch containing both oxybutynin base and xanomeline base in the same reservoir or matrix.

Said TTS may also be a patch divided in two parts, concurrently releasing the aforementioned oxybutynin daily amounts and, respectively, the aforementioned xanomeline amounts, in admixture with the common solvents, polymers or co-polymers and permeation enhancers.

Similarly, the non-occlusive transdermal therapeutic systems, in particular the gel formulations and the spray formulations contain oxybutynin or a pharmaceutically acceptable salt thereof, in association with xanomeline or a pharmaceutically acceptable salt thereof; and release the aforementioned oxybutynin amounts associated with the aforementioned xanomeline amounts, in admixture with the common solvents, carriers and permeation enhancers.

The following examples are included for illustrative purposes only, and are not intended to limit the scope of the invention.

Example 1

Study 1—Establishment of the Dose-Response to Xanomeline in a Mouse Model of Diarrhea.

Male Swiss mice (4-6 weeks old), N=10 per treatment group were used, and treated intra-peritoneally (i.p.) with either vehicle (vehicle group) or increasing doses of xanomeline, a representative muscarinic agonist. Mice were randomly assigned to one of two experimental groups (vehicle; or increasing doses of xanomeline). Each animal was identified by its group name, cage number, series (day) of experiment, and number (1 to 10) written with permanent ink on the tail. Mice were placed individually in cages without any bedding materials. During the experiment the number of fecal pellets were counted at different time-points, starting one hour before the time of the administration of the test compound (T0), as outlined below:

T−1 h to T0: counting of the accumulated fecal pellets excreted.

T0: administration of the test compound.

T0 to T+2 h: counting of the accumulated fecal pellets excreted.

T+2 h to T+4 h: counting of the accumulated fecal pellets excreted.

The total number of fecal pellets for each mouse was counted over time. An analysis of variance (ANOVA) was performed on the results. Fisher's Protected Least Significant Difference was used for pairwise comparisons; p values≤0.05 were considered significant. Grubbs' test (http (hypertext transfer protocol) www at graphpad.com/quick-calcs/Grubbs1.cfm) was used to detect outliers for each parameter in each experimental group.

Results confirmed that xanomeline i.p. (0.3 to 30 mg/kg) dose-dependently causes diarrhea.

Study 2—Antagonism of Xanomeline-Induced Diarrhea in Mice by Oxybutynin

Male Swiss mice (4-6 weeks old), N=10 per treatment group were used. Animals were pretreated with i.p. oxybutynin (a representative peripheral muscarinic receptor antagonist) or vehicle; 30 minutes later animals were treated with xanomeline at a dose of 30 mg/kg that caused diarrhea (as determined in Experiment 1). The dose of oxybutynin ordinarily ranged from 0.3 to 30 mg/kg.

Mice were placed individually in cages without any bedding materials. During the experiment the number of fecal pellets was counted at different time-points as outlined below:

T−1 h to T0: counting of the accumulated fecal pellets excreted.

T0: administration of oxybutinin.

T30 min: administration of vehicle or xanomeline.

T 30 min to T 2.5 h: counting of accumulated fecal pellets excreted.

T+2.5 h to T+4.5 h: counting of accumulated fecal pellets excreted.

The total number of fecal pellets for each mouse was counted over time. An analysis of variance (ANOVA) was performed on the results. Fisher's Protected Least Significant Difference was used for pairwise comparisons. The p value≤0.05 were considered significant. Grubbs' test (http (hypertext transfer protocol) www at graphpad.com/quick-calcs/Gnibbs1.cfm) was used to detect outliers for each parameter in each experimental group.

Results showed that oxybutynin dose-dependently antagonized the diarrhea induced by xanomeline, thus confirming that the representative nsPAChA oxybutynin suppresses the adverse effects of the representative muscarinic antagonist xanomeline.

Example 2

Evaluation of Cognition with Oxybutynin and Xanomeline in the T-maze Alternation Task in Mice The T-maze continuous alternation task (T-CAT) is useful as model for studying compounds with cognitive enhancing properties. The T-maze consists of 2 choice arms and 1 start arm mounted to a square center. Manual doors are provided to close specific arms during the force choice alternation task.

Male Swiss mice (4-6 weeks old), N=10 per treatment group were used, and were pre-treated with:

Oxybutynin at the dose that blocked fecal pellet excretion in Study 2 of Example 1.

Thirty minutes later mice were treated with either vehicle or one of 4 doses of xanomeline:

the highest dose that did not cause diarrhea;

a dose that caused diarrhea.

Mice were randomly assigned to one of the different experimental treatment groups. Each animal was identified by its group name, cage number, series (day) of experiment, and number (1 to 10) written with permanent ink on the tail.

The T-maze apparatus is made of gray Plexiglas with a main stem (55 cm long×10 cm wide×20 cm high) and two arms (30 cm long×10 cm wide×20 cm high) positioned at 90 degree angle relative to the main stem. A start box (15 cm long×10 cm wide) is separated from the main stem by a guillotine door. Horizontal doors are also provided to close specific arms during the force choice alternation task.

The experimental protocol consisted of one single session, which started with 1 "forced-choice" trial, followed by 14

"free-choice" trials. In the first "forced-choice" trial, animals were confined for 5 seconds to the start arm and then were released while either the left or the right goal arm was blocked by the horizontal door. Animals then negotiated the maze, eventually entering the open goal arm, and returned to the start position. Immediately after the return of the animals to the start position, the left or right goal door was opened and the animals were allowed to choose freely between the left and right goal arm ("free choice trials). An animal was considered as having entered in arm when it placed its four paws in the arm. A session was terminated and animals were removed from the maze as soon as 14 free-choice trials had been performed or 10 min had elapsed, whichever event occurred first.

The apparatus was cleaned between each animal using 40% ethanol. Urine and feces were removed from the maze. During the trials, animal handling and the visibility of the operator was minimized as much as possible.

The percentage of alternation over the 14 free-choice trials was determined for each mouse and was used as an index of working memory performance. This percentage is defined as entry in a different arm of the T-maze over successive trials (i.e., left-right-left-right, etc). Analysis of variance (ANOVA) was performed on the results. Fisher's Protected Least Significant Difference was used for pairwise comparisons. p values≤0.05 were considered significant. The drug-induced improvement of memory was calculated by setting the respective response of the saline/vehicle as 100% and that of the test group as 0% reversion. Grubbs' test (http (hypertext transfer protocol) www at graphpad.com/quickcalcs/Grubbs1.cfm) was used to detect outliers for each parameter in each experimental group.

Results showed a dose-dependent increase in performance in the T-maze in animals treated with i.p. xanomeline. At the higher dose, however, animals were too sick to perform the test. Pretreatment with i.p. oxybutynin restored the animals' ability to perform the T-maze test.

The invention claimed is:

1. A method for treating Alzheimer type dementia, which comprises administering to a patient in need of said treatment a muscarinic receptor agonist selected from the group consisting of xanomeline and pharmaceutically acceptable salt thereof, in combination with a transdermal therapeutic system comprising oxybutynin or a pharmaceutically acceptable salt thereof; wherein said transdermal therapeutic system releases oxybutynin at a rate of 3.9 mg/24 hr.

2. The method of claim 1, wherein said transdermal therapeutic system incorporates said oxybutynin into a patch.

3. A transdermal therapeutic system comprising oxybutynin or a pharmaceutically acceptable salt thereof, for use in the treatment of Alzheimer type dementia, in combination with a muscarinic receptor agonist selected from the group consisting of xanomeline and pharmaceutically acceptable salts thereof; wherein said transdermal therapeutic system releases oxybutynin at a rate of 3.9 mg/24 hr.

4. A transdermal therapeutic system comprising oxybutynin or a pharmaceutically acceptable salt thereof, in combination with xanomeline or a pharmaceutically acceptable salt thereof; wherein said transdermal therapeutic system releases oxybutynin at a rate of 3.9 mg/24 hr.

* * * * *